(12) United States Patent
Blondel et al.

(10) Patent No.: US 8,129,402 B2
(45) Date of Patent: *Mar. 6, 2012

(54) SCREENING MOLECULES WITH ANTI-PRION ACTIVITY: KITS, METHODS AND SCREENED MOLECULES

(75) Inventors: Marc Blondel, Saint-Pol de Leon (FR); Christophe Cullin, Merignac (FR); Jean Michel Vierfond, Maisons Alfort (FR); Stephane Bach, Saint-Pol de Leon (FR); Nicolas Talarek, Talence (FR); Yvette Mettey, Poitiers (FR)

(73) Assignees: Centre National de la Recherche Scientifique, Paris (FR); Universite Victor Segalen Bordeaux 2, Bordeaux (FR); Universite de Poitiers, Poiters (FR)

( * ) Notice: Subject to any disclaimer, the term of this patent is extended or adjusted under 35 U.S.C. 154(b) by 1087 days.

This patent is subject to a terminal disclaimer.

(21) Appl. No.: 10/531,594

(22) PCT Filed: Oct. 20, 2003

(86) PCT No.: PCT/FR03/03101
§ 371 (c)(1),
(2), (4) Date: Nov. 28, 2005

(87) PCT Pub. No.: WO2004/035813
PCT Pub. Date: Apr. 29, 2004

(65) Prior Publication Data
US 2006/0172337 A1 Aug. 3, 2006

(30) Foreign Application Priority Data
Oct. 18, 2002 (FR) .................................... 02 13022
Jul. 7, 2003 (FR) .................................... 03 08289

(51) Int. Cl.
*A61K 31/44* (2006.01)
(52) U.S. Cl. ....................................................... 514/298
(58) Field of Classification Search ........................ None
See application file for complete search history.

(56) References Cited

U.S. PATENT DOCUMENTS

| 3,758,479 | A | 9/1973 | Schmutz et al. |
| 4,024,242 | A | 5/1977 | Hungerer |
| 5,695,782 | A | 12/1997 | Bourquin |
| 6,479,504 | B1 | 11/2002 | Macfarlane et al. |

FOREIGN PATENT DOCUMENTS

| WO | WO 99/29891 A | 6/1999 |
| WO | WO 02/065136 A | 8/2002 |

OTHER PUBLICATIONS

Donnelly et al. "Cyclizations. Part I. Electrochemical and photochemical reactions of 1-(4-fluorophenyl)-5-(2-halogenophenyl)tetrazoles" Journal of the Chemical Society, Perkin Transactions 1: Organic and Bio-Organic Chemistry (1972-1999) (1993), (14), 1557-62.*
Cookson et al. "Polycyclic Fused Amidines . . . " Journal of the Chemical Society, Perkin Transactions 1: Organic and Bio-Organic Chemistry (1972-1999) (1975), (19), 1850-1854.*
Geschwind et al. Protein Misfolding in Neurodegenertive Diseases (2008) p. 517-543 Eds: Smith, Simon and Sewell (CRC Press: Boca Raton, FL).*
Baret et al. J. Virology (Aug 2003) 77(15); 8462-8469.*
Zou et al. (2004) Drug Discovery Today: Disease Models 1(2): 157-164.*
Groschup et al. Vet. Res. (2008) 39:32 (pp. 1-13) (electronic journal; www.vetres.org, downloaded Jul. 7, 2009).*
Le et al. J. Biochem. Toxicology (1996) 11(6): 297-303.*
Cavier, R. European J. Med. Chem. (1966) 66(5-6): 327-330 with English translation.*
Mettey, Y., et al., "*Synthesis of 11-Aminodibenzo 'b,f]thiazepines and Fluoro Derivatives*," 34 Heterocyclic Chem. 465-467 (1997); XP009008912.
Kessar, S.V., et al., "*New Routes to Condensed Polynuclear Compounds, II Direct Benzyne Cyclisation of N-Chlorobenzylidene Arylamines*," Tetrahedron Letters 1155-1156 (1969); XP009009071.
"*Acridine and phenothiazine derivatives a pharmacotherapeutics for prion disease*," 98(17) Proceedings of the National Academy of Sciences of the United States 9836-9841 (Aug. 14, 2001): XP002237386, Korth et al.
Astrid Lunkes et al., "A Cellular Model that Recapitulates Major Pathogenic Steps of Huntington's Disease," Human Molecular Genetics, 1998, vol. 7, No. 9, pp. 1355-1361.
Erwann Rousseau, "Targeting Expression of Expanded Polyglutamine Proteins to the Endoplasmic Reticulum or Mitochondria Prevents Their Aggregation," PNAS, Jun. 29, 2004, vol. 101, No. 26, pp. 9648-9653.
Astrid Lunkes et al., "Proteases Acting on Mutant Huntingtin Generate Cleaved Products that Differentially Build Up Cytoplasmic and Nuclear Inclusions," Molecular Cell, Aug. 2002, vol. 10, pp. 259-269. E. Fernandez-Bellot et al., "The Protein—Only Theory and the Yeast *Saccharomyces cerevisiae*: the Prions and the Propagons" CMLS Cell Mol. Life Sci. (2001) 58:1857-1878, Birkhauser Vering, Basel, Switzerland.
Deborah Tribouillard-Tanvier et al., "Antihypertensive Drug Guanabenz is Active in vivo Against Both Yeast and Mammalian Prions," (2008) PLoS One, 3(4):1-9, e1981.
Deborah Tribouillard-Tanvier et al., "Protein Folding Activity of Ribosomal RNA is a Selective Target of Two Unrelated Antiprion Drugs," PLoS One, 3(5):1-14, e2174, (2008).
Deborah Tribouillard-Tanvier et al., "Using Budding Yeast to Screen for Anti-Prion Drugs", (2006) Biotechnology Journal, 1:58-67.
Deborah Tribouillard-Tanvier et al., "Antiprion Drugs as Chemical Tools to uncover mechanisms of Prion Propagation," (2007) Prion, 1(1): 48-52.

(Continued)

*Primary Examiner* — James D Anderson
(74) *Attorney, Agent, or Firm* — Buchanan Ingersoll & Rooney P.C.

(57) ABSTRACT

The invention concerns screening molecules with anti-prion activity. More particularly, it concerns kits for screening molecules with anti-prion activity characterized in that they comprise in combination a [PSI+], phenotype yeast, an antibiogram and an agent for purifying prions at sub-efficient doses, said yeast including the ade1-14 allele of the ADE1 gene and an inactivated ERG6 gene, the screening methods, and a family of molecules with anti-prion activity isolated by the inventive screen. The invention is applicable to anti-prion agents for producing medicines in particular for treating neurodegenerative diseases involving protein aggregates.

3 Claims, 6 Drawing Sheets

OTHER PUBLICATIONS

Figure 1:
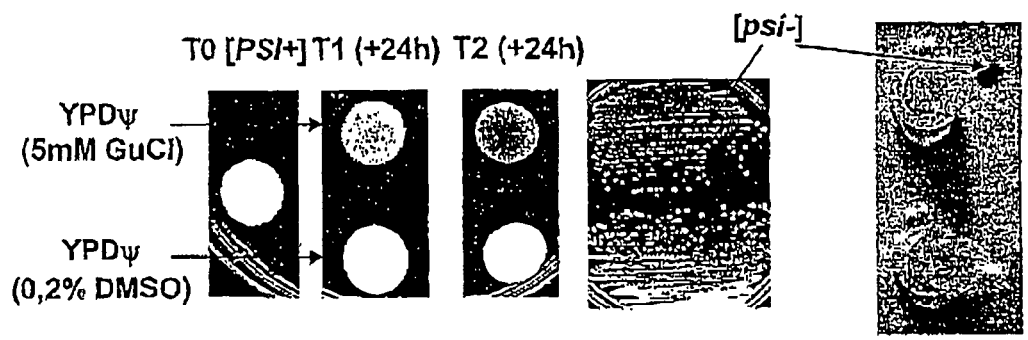

Stephane Bach et al., "Isolation of Drugs Active Against Mammalian Prions Using a Yeast-based Screening Assay," Nature Biotechnology (2003) 21(9):1075-1081.

Kazutoshi Shindo et al., "Oxygenation Reactions of Various Tricyclic Fused Aromatic Compounds using *Escherichia coli* and *Streptomyces lividans* Transformants Carrying Several Arene Dioxygenase Genes," Biosci. Biotechnol. Biochem. 65 (11), 2472-2481 (2001).

International Search Report dated Jun. 3, 2004 issued in corresponding PCT/FR03/03101.

Weissman, J., et al., "*Mechanism of Amyloid formation and propagation: Lessons from a yeast prion*," 80(1) Biophysical Journal 329a (Jan. 2001); XP002237383.

Wickner, R. B., et al., "*Prions of yeast, 'PSI! and 'URE3!, as models for neurodegenerative diseases*," 61 Cold Spring Harbor Symposia on Quantitative Biology 541-550 (1996); XP001098910.

Talloczy, Z., et al., "*The (KIL-d) element specifically regulates viral gene expression in yeast*," 155(2) Genetics 601-609 (Jun. 2000); PREV200000387721; XP002237388.

Emter, R., et al., "*ERG6 and PDR5 regulate small lipophilic drug accumulation in yeast cells via distinct mechanisms*," 521(1-3) Febs Letters 57-61 (Jun. 19, 2002); XP002237387.

Crowley, J.C., et al., "*Molecular cloning of chromosome I DNA from Saccharomyces cerevisiae: Isolation of the ADE1 gene*," 159(1) Journal of Bacteriology 1984 United States 413-417 (1984); EMB-1984159946; XP002273243.

Bach et al., "Isolation of Drugs Active Against Mammalian Prions Using a Yeast-Based Screening Assay" *Nature Biotechnology* vol. 21, No. 9 (Sep. 2003) p. 1075-1081.

Barbezier et al. "Antiprion Drugs 6-aminophenanthridine and Guanabenz Reduce PABPN1 Toxicity and Aggregation in Oculopharyngeal Muscular Dystrophy" *EMBO Mol Med* vol. 3 p. 35-49 (2011).

Tribouillard et al., "Using Budding Yeast to Screen for Anti-prion Drugs" *Biotechnology Journal* (2006) vol. 1, p. 58-67.

Tribouillard et al., "Antihypertensive Drug Guanabenz is Active in Vivo Against both Yeast and Mammalian Prions" *PLOS One* (Apr. 2008) vol. 3, Issue 4 p. 1-9.

* cited by examiner

Wells 1 to 3: KPI - 5 µM
Wells 6: DMSO solvent (0.01%)

Wells 4, 5, 10, 11: untreated cells
Wells 7 to 9: chlopromazine - 5 µM

SCREENING MOLECULES WITH ANTI-PRION ACTIVITY: KITS, METHODS AND SCREENED MOLECULES

This application is a U.S. National Stage of International Application No. PCT/FR2003/003101, filed Oct. 20, 2003, and published on Apr. 29, 2004, as WO 2004/035813. This application claims priority to French Patent Applications Nos. FR02/13022, filed Oct. 18, 2002, and FR03/08289, filed Jul. 7, 2003, hereby incorporated by reference for all purposes.

The present invention relates to screening of molecules with anti-prion activity. It relates more particularly to kits for screening molecules with anti-prion activity, methods of screening, and a family of molecules with anti-prion activity revealed using the screen according to the invention.

Prions are infectious proteins responsible for certain neuro-degenerative diseases of spongiform encephalopathy type in mammals, such as Creutzfeldt-Jakob's disease in humans or also the so-called "mad cow disease" in bovines or "scrapie" in ovines. These different diseases are caused by unconventional infectious agents: unlike traditional infectious agents (bacteria, viruses for example), they contain no nucleic acids. Professor Stanley Prusiner formulated the "protein-only" hypothesis, according to which the infectious agent would be constituted only by a protein. This protein exists naturally in cells in a normal (or $PrP^c$) form, i.e. soluble, essentially in the form of an α helix and non-aggregated, therefore functional. Under certain still unknown conditions, this protein can be converted to a prion (or $PrP^{sc}$) form. In this prion form, the protein forms insoluble aggregates, essentially in the form of β sheets. The infectious character of this $PrP^{sc}$ prion conformation would result from the fact that, apart from the characteristics indicated previously, the protein in prion form also gains the ability to catalyze the passage from the normal $Prp^c$ cell form to the $PrP^{sc}$ prion form in a "snowball"-type mechanism. Baker's yeast *Saccharomyces cerevisiae* contains several proteins that behave like prions (Fernandez-Bellot and Cullin, 2001). Since as long ago as the 1960s, two unconventional genetic mechanisms have been described. In 1994, the corresponding [PSI+] and [URE3] phenotypes were proposed as resulting from the autocatalytic inactivation of the Sup35p and URE2p proteins respectively. These prion proteins therefore have a priori a mechanistic analogy with mammal systems deleterious to public health. Like the PrP protein, the "normal" Sup35p protein passes from a soluble state to an insoluble and aggregated state as soon as the protein is in contact with another Sup35p protein in prion form. This aggregated state is verified both by centrifugation experiments and by intracellular localization experiments. Yeast prions can be eliminated ("cured") by a strong dose (1 to 5 mM) of guanidium chloride. As a result of such a treatment (which must applied to at least six to ten generations), the protein aggregates generated by the presence of the prions disappear and the protein in question (Sup35p, for example) is found in a normal, soluble, functional form but having retained the capability of being converted to a prion form should it again come into contact with another Sup35p protein in such a state.

The Sup35p protein, in a heterodimeric complex with the Sup45p protein, forms a translation termination factor. This factor recognizes the opal stop codons (UGA). In its normal cell form (soluble and active) in the [psi−] strains, Sup35p, in combination with Sup45p effectively terminates translation at the level of these opal codons. In a [PSI+] strain where the Sup35p protein is in prion form, it is mostly present in the form of insoluble aggregates. Being unable to bind to Sup45p, it is thus non-functional in the translation termination. A small fraction of all of the cellular Sup35p proteins however remains soluble in these [PSI+] cells where it makes it possible, in a complex with Sup45p, to ensure a "minimum translation termination service", a service essential to the survival of the yeast. A colorimetric system making it possible to detect, in an indirect fashion, the form in which the Sup35p protein is present: normal or prion, has been produced from these findings. This system, which has been described for a long time (see the article on synthesis by Fernandez-Bellot and Cullin, 2001), is based on the use of the adel-14 allele of the ADE1 gene, coding for an enzyme of the adenine biosynthesis route: SAICAR synthetase. This enzyme catalyzes the formation of 4-(N-succinocarboxamide)-5-aminoimidazole ribonucleotide (SAICAR) from 4-carboxy-5-aminoimidazole ribonucleotide (CAIR). The adel-14 allele contains an opal codon in the reading frame of the ADE1 gene. In a [psi−] strain, Sup35p in combination with Sup45p will therefore stop the translation of the ADE1 gene at the level of this stop codon. The protein adel-14p thus translated will be truncated and therefore non-functional. As a result the substrates upstream of the Ade1p enzyme will accumulate, in particular the 5-aminoimidazole ribonucleotide (AIR) The AIR being oxidized to a red-coloured compound, the colonies formed by the [psi−]. cells will be red in colour. Moreover, these cells will be auxotrophic for adenine. Conversely, in a [PSI+] strain, the protein Sup35p is essentially present in the form of aggregates therefore incapable of being combined with Sup45p in order to stop translation at the level of the opal codon of the adel-14 allele of the ADE1 gene. As a result, the ribosomes will pause at the level of this stop codon before resuming their translation activity (readthrough). A certain quantity of functional Ade1p protein will therefore be synthesized, the cells will be autotrophic for adenine and will form white to pink-coloured colonies.

In an article which appeared in P.N.A.S, Prof. Stanley Prusiner's team discloses a test for detecting molecules with anti-prion activity (Korth et al., 2001). This test is carried out on a mammal model (murine neuroblastomas infected with $PrP^{sc}$) The safety conditions (P3 laboratory) and cell culture conditions (significant handling) do not allow high-throughput screening to be carried out.

The Application WO 98/30909 also describes a process for screening molecules with anti-prion activity carried out on rodents infected with an unconventional transmissible agent. This screening method has the same limits as the method described in P.N.A.S.

The inventors' work has led them to produce a high-throughput screening system in order to detect molecules possessing an anti-prion activity, based on the calorimetric reporter system of the protein Sup35p, described above.

The present invention therefore relates to a kit for screening molecules with an anti-prion activity, characterized in that it comprises in combination a yeast of phenotype [PSI+], an antibiogram and a prion curing agent in sub-effective doses, said yeast having the adel-14 allele of the ADE1 gene as well as an inactivated ERG6 gene.

Although based on yeast prions, the kit according to the invention makes it possible to isolate molecules active against mammal prions. Example 7 below shows that the most active molecules isolated by Prof. Prusiner also have an activity in the screen according to the invention.

However, numerous differences are observed between yeast prions and mammal prions. In an article in the journal "Cellular and Molecular Life Sciences", Professor C. Cullin proposes, even in view of these differences, distinguishing yeast prions from mammal prions by using the term "propagons". As particular differences between "prions" (mammal) and "propagons" (yeast), there can be mentioned the cytoplasmic character of propagons whereas the mammal PrP prion is a protein anchored to the plasmic membrane, the pathological character of mammal prions, as well as a certain number of biophysical differences (ternary and quaternary structure, reversibility of the curing etc.)

One of the main advantages of such a screen resides in its complete harmlessness which allows it to be carried out in a standard level L2 molecular biology laboratory, and not, as required in the previous techniques, in a level P3 laboratory.

Moreover, the great ease of use and very low cost of this kit make it possible carry out high-throughput screening. The use of antibiogram pellets, which allow the diffusion of the product by creating a concentration gradient, moreover makes it possible to test a multiplicity of concentrations in a single experiment, unlike the standard tests, in which only one concentration is tested. For each molecule the anti-prion activity of which is tested, the use of the antibiogram also makes it possible to acquire information on the toxicity of the product as well as on the activity/concentration ratio, and thus to determine the best effective concentration.

The [PSI+] strain used in the kit according to the invention carries an inactivation of the ERG6 gene. In fact, yeasts are naturally fairly impermeable. In particular, the preferred yeast for implementing the invention, *Saccharomyces cerevisiae*, has an impermeability such that the carrying out of a screening process proves particularly ineffective without this inactivation.

The screen analysis method according to the invention is visual thanks to the use of the adel-14 allele. According to the anti-prion activity of the molecule tested, the colonies of cells will have a red, pink or white staining. The choice of the strain of yeast can make it possible to improve the contrast between the colonies. In fact, certain so-called "Strong" strains facilitate visual analysis of the screen. Such strains possess a strong level of aggregation of the prion forms. In the opposite case, the strain is referred to as "Weak". The strains preferred for implementation of the invention are therefore the "Strong"-type strains.

Other yeasts can also be used. As examples there can be mentioned: *Kluyveromyces lactis, Pichia methanolica, Saccharomyces ludwigii, Kluyveromyces marxianus, Pichia pastoris, Zygosaccharomyces rouxi, Schizosaccharomyces pombe*.

Given the synthetic lethality observed between the inactivation of the ERG6 gene and the inactivation of the TRP1 gene, the ERG6 gene can be deleted using the TRP1 gene as deletion marker.

Advantageously, the kit moreover comprises a prion curing agent at sub-effective doses.

By curing, is meant an elimination of the prion forms from the yeast cells. This elimination can be temporary or permanent.

By way of example, a prion curing agent can be hydrogen peroxide or preferentially, guanidium chloride.

By sub-effective doses, is meant doses which used alone would not suffice to eliminate the prions from the yeasts. The values of such doses are given, in the examples which follow, for guanidium chloride.

The benefits of the presence of a curing agent at sub-effective doses are to reinforce the sensitivity of the screen and obtain a better contrast.

The kit according to the invention can be used in a method for screening molecules with anti-prion activity. This screening method, to which the invention also relates, is characterized in that it uses a [PSI+] phenotype yeast having the adel-14 allele of the ADE1 gene as well as an inactivated ERG6 gene and comprises the following stages:

a. production of a lawn of cells in vitro on a medium complemented with a sub-effective dose of a prion curing agent,
b. deposition of the compounds to be tested according to the antibiogram method,
c. incubation for approximately 2-4 days at approximately 20-25° C., and,
d. analysis of the staining of the cell colonies.

This method possesses advantages analogous to those of the kit according to the invention. It is a visual test, very easy to analyze. Its implementation is very simple and inexpensive. The precautions relative to safety are those of a standard molecular biology laboratory. It allows mass screening: a single person can manually screen more than 400 products per day. Very high-throughput screening would be possible by automation of the method. The screen result is developed after 7 days, without it being necessary to resort to a lot of handling between day D and day D+7 (optionally a change in temperature of the incubator). Finally, this method is particularly economical.

One of the yeasts preferred for the implementation of this method is *Saccharomyces cerevisiae*.

Advantageously, the curing agent of Stage a. is guanidium chloride.

The method can also comprise the following stages:

e. incubation for approximately 2-4 days at approximately 2-6° C., and/or,
f. carrying out a secondary screening test.

The incubation at 2-6° C. makes it possible to accentuate the contrast in staining of the colonies.

Preferentially, the secondary screening test can comprise the following stages:

construction of a strain of yeast in which the ADE2 gene is under the control of the DAL5 gene promoter carrying out Stages a. to e. of the methods described above.

Such a secondary screening makes it possible to test very rapidly whether the molecules isolated during the primary screening can have a general effect on the prions in the yeast. In fact, the SUP35 genes (responsible for the [PSI+] prion) and URE2 (responsible for the [URE3] prion) code for enzymes having totally different functions and the primary sequences of which are very remote.

The invention also covers the molecules isolated by the screening method according to the invention.

In particular, the screening method has made it possible to isolate anti-prion agents having the following formula (I):

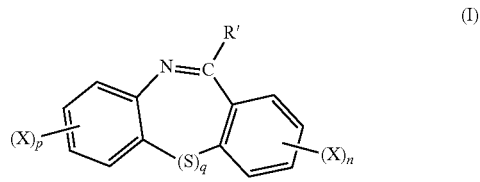

in which R is an H, $NH_2$, $NHR^2$ group, where $R^2$ is an alkyl or alkylaminoalkyl chain with 1 to 10 carbon atoms, branched or unbranched, X represents F, Cl, Br, I, $CF_3$, $SR^3$, $OR^3$, OH, $NO_2$, $COR^3$, $CONH_2$, COOH, $COOR^3$, where $R^3$ is an alkyl group with 1 to 4 carbon atoms, preferably $CH_3$.

p and n, identical or different, are equal to 0, 1 or 2, q is equal to 0 or 1.

The invention relates in particular to the anti-prion agents of formula (III):

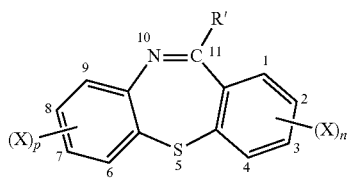

(III)

in which R' represents an H, $NH_2$, $NH-(CH_2)_3-N(CH_3)_2$, $NH-CH(CH_3)-(CH_2)_3-N(CH_2-CH_3)_2$ group,
X represents F, Cl, $CF_3$,
p and n, identical or different, are equal to 0, 1 or 2.

This family of molecules, called "Kastellpaolitines" by the inventors, possesses the sought anti-prion activity to a greater or lesser degree. In particular, the chlorinated derivatives of this family are particularly effective. The best effectivenesses are obtained when chlorine is placed in position 2, 3 or 4, preferably in position 4 (see KP1 in the examples which follow).

The invention relates more particularly to the compounds of formula (II):

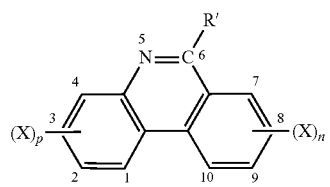

(II)

in which R' represents an H, $NH_2$, $NH-(CH_2)_3-N(CH_3)_2$, $NH-CH(CH_3)-(CH_2)_3-N(CH_2-CH_3)_2$ group,
X represents F, Cl, $CF_3$,
p and n, identical or different, are equal to 0, 1 or 2.
for use as a medicament, and in particular, as an anti-prion agent.

It also relates to the pharmaceutical compositions comprising a therapeutically effective quantity of at least one compound of formula (II) in which:

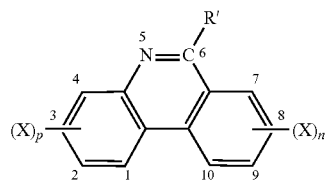

(II)

R' represents an H, $NH_2$, $NH-(CH_2)_3-N(CH_3)_2$, $NH-CH(CH_3)-(CH_2)_3-N(CH_2-CH_3)_2$ group,
X represents F, Cl, $CF_3$,
p and n, identical or different, are equal to 0, 1 or 2.
in combination with at least one pharmaceutically acceptable vehicle.

Certain compounds of this family are particularly active. These are phenanthridine and 6-aminophenanthridine, as well as their chlorinated derivatives, in particular when the chlorine is placed in position 8, 9 or 10, preferably in position 10 (see in the examples which follow).

Preferentially, in formulae (II) and (III), R' represents $NH_2$. In fact, a very good activity of the molecules has been noted when R' represents $NH_2$.

The invention also proposes a method for treating neurodegenerative diseases involving protein aggregates, comprising a stage of administering to an animal or to a patient a therapeutically effective quantity of at least one of the compounds of formula (I), (II) or (III) according to the invention.

The anti-prion agents according to the invention are particularly useful for obtaining a medicament intended to prevent and/or to treat neurodegenerative diseases, in particular of the protein-aggregation type, such as the spongiform encephalopathies, Alzheimer's (tau), Parkinson's (α-synuclein) and Huntington's (huntingtin) disease etc. These medicaments can be intended for human or veterinary use, in particular for domestic (cows, sheep etc.) or wild animals (lynx, the Cervidae such as deer, moose etc.).

Figure 2:
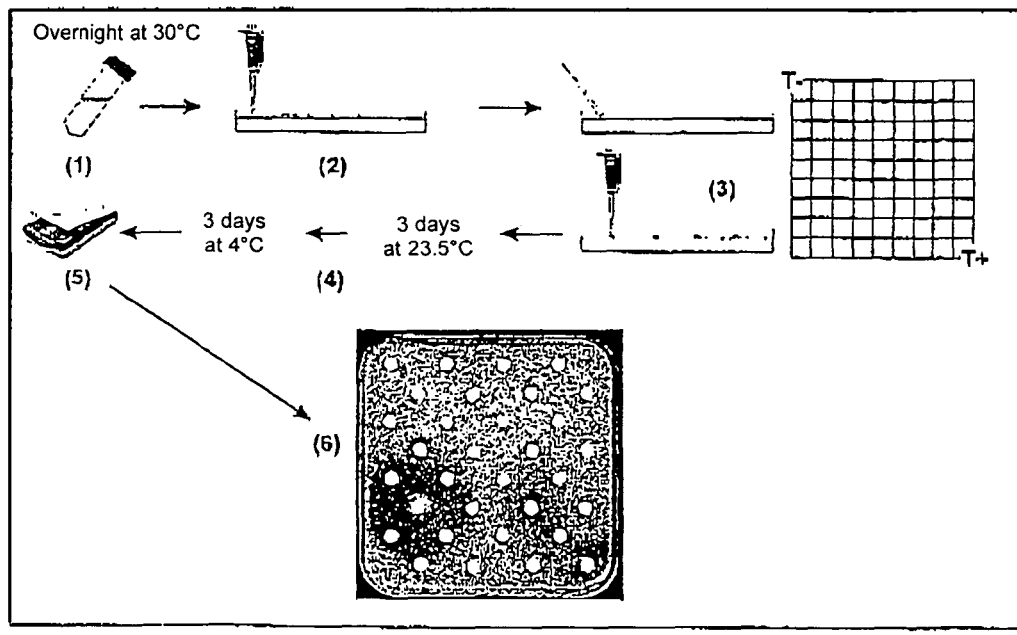
Figure 3:
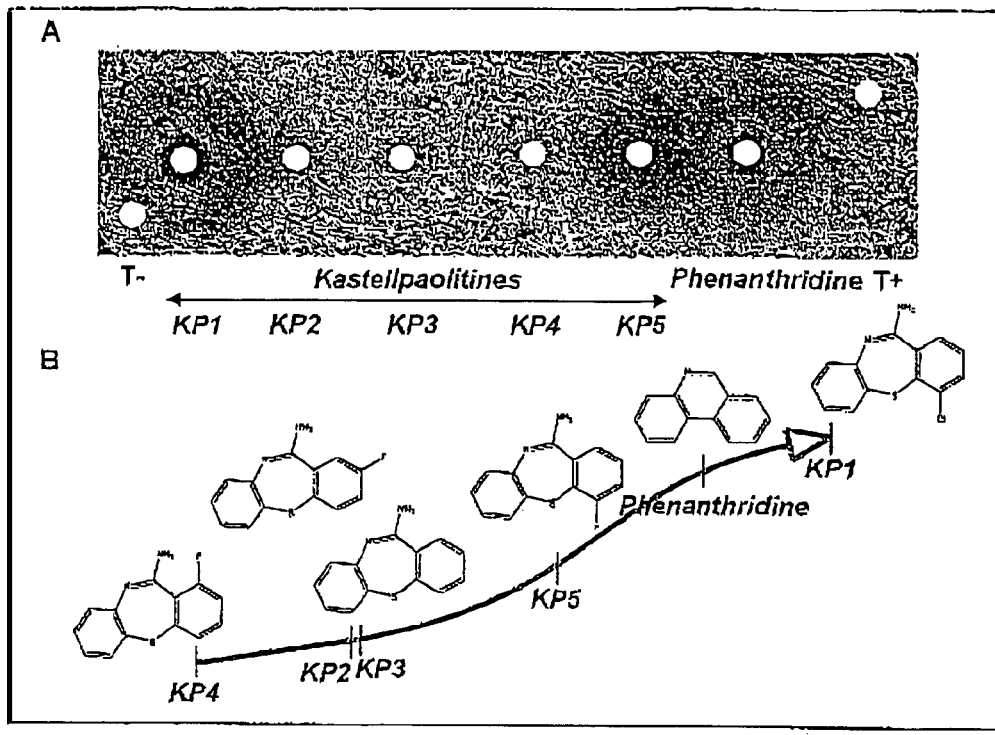
Figure 4:
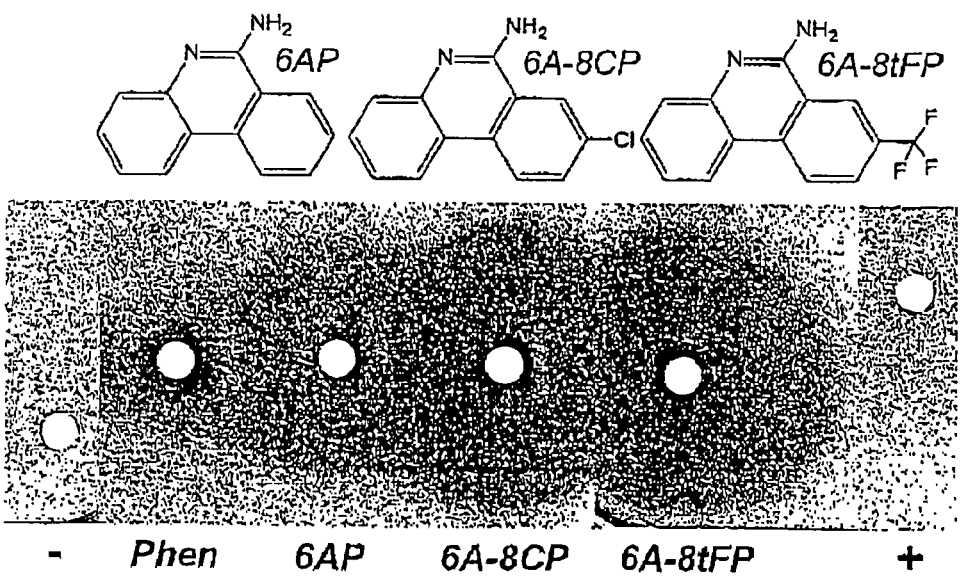
Figure 5:
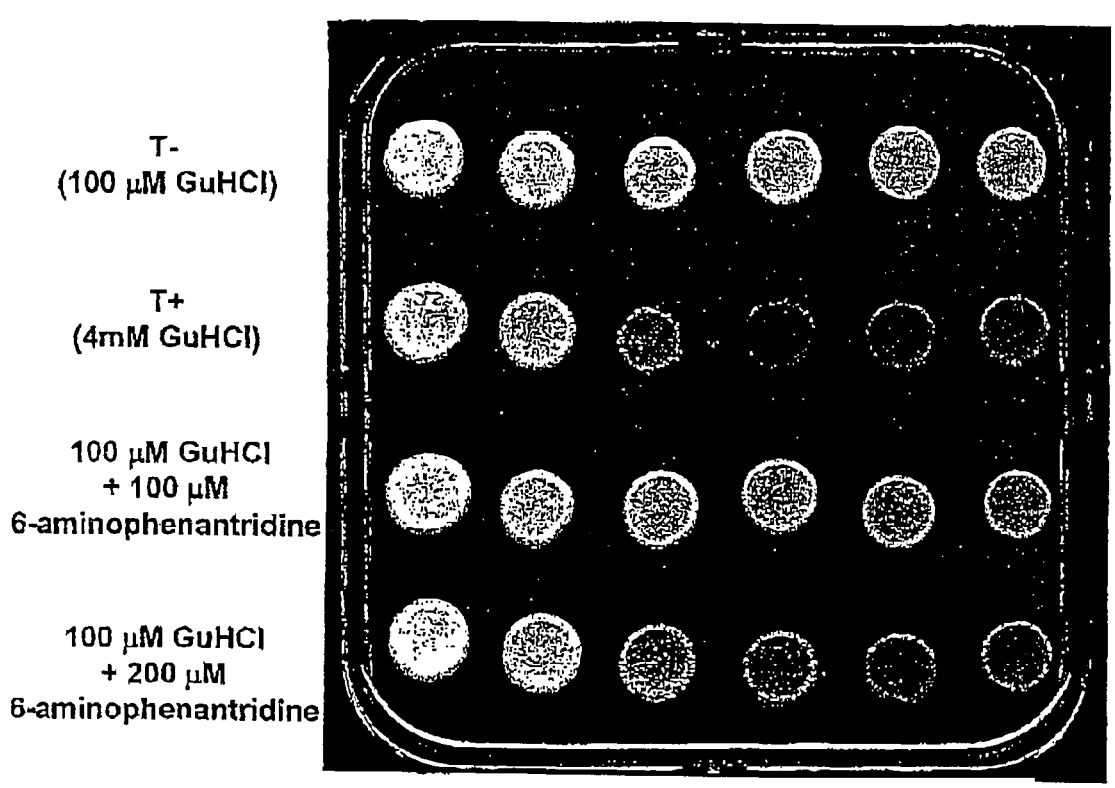
Figure 6:
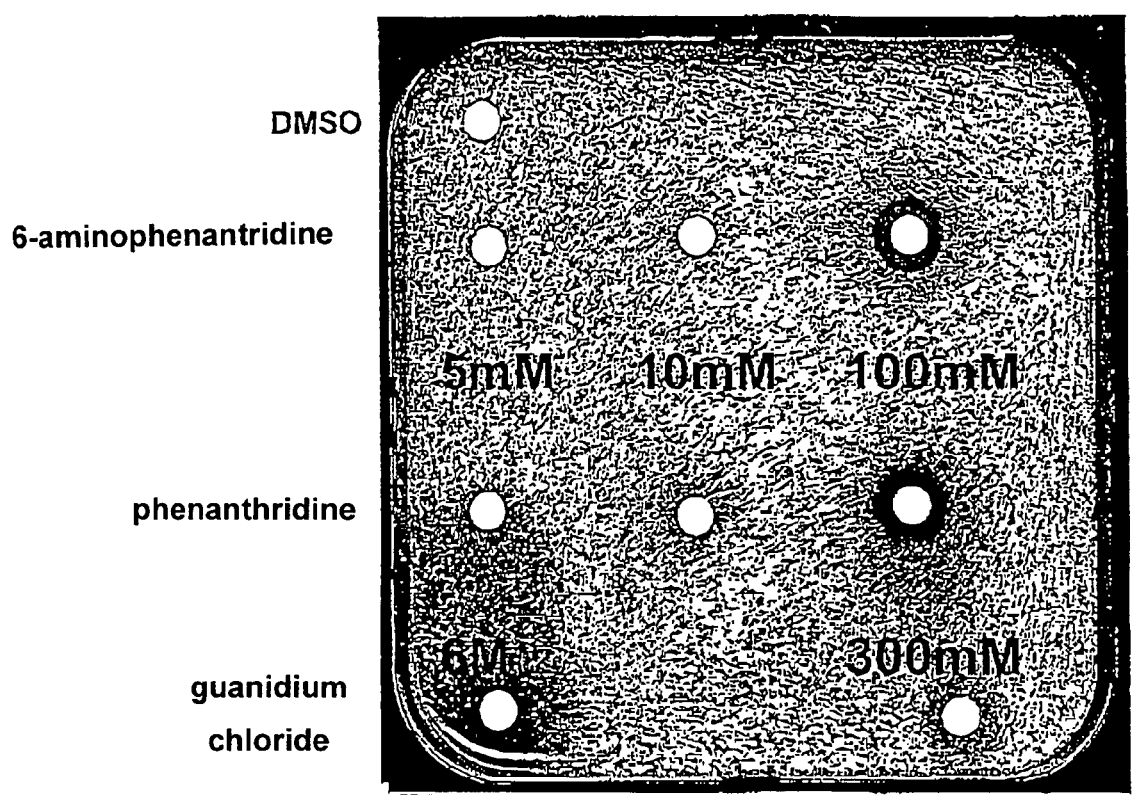
Figure 7:
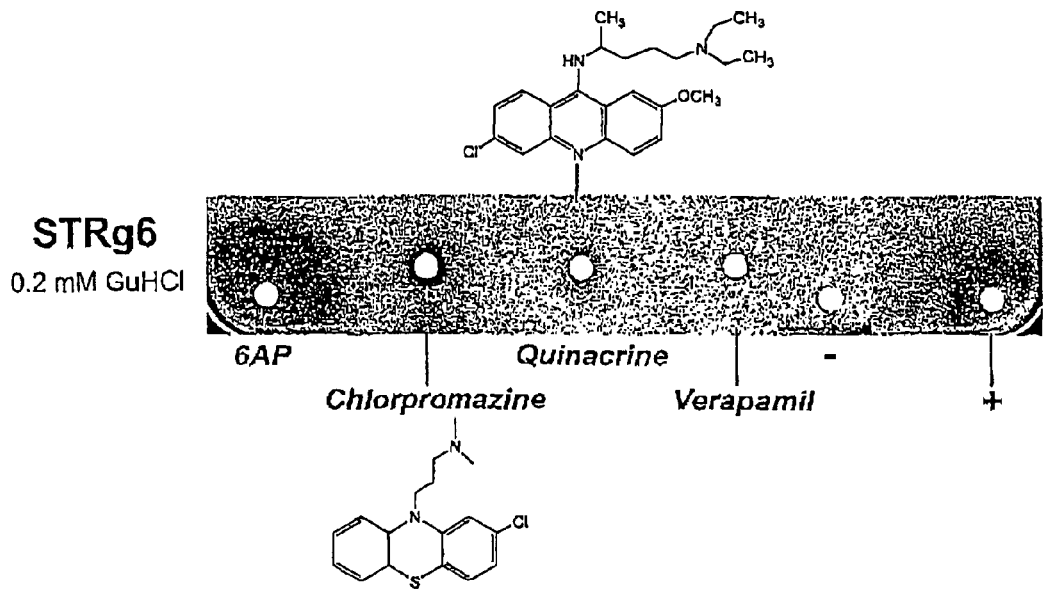
Figure 8:
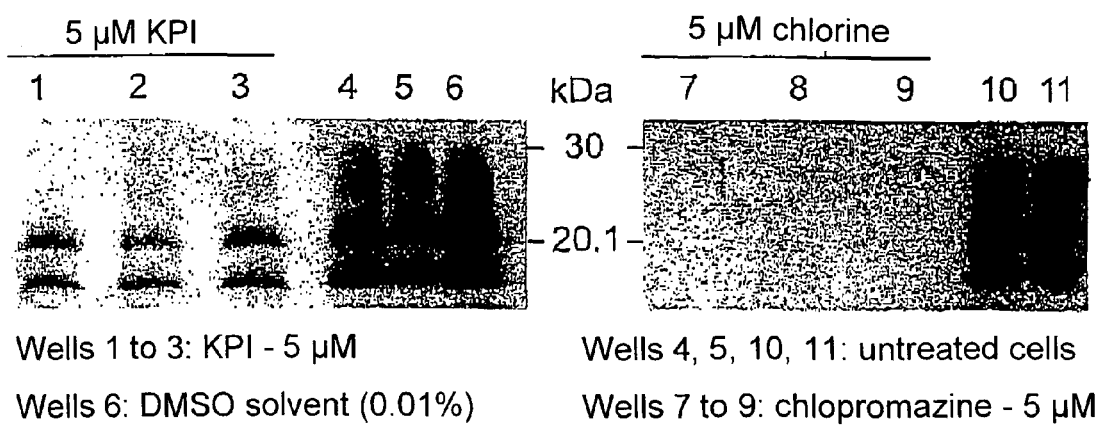
Figure 9:
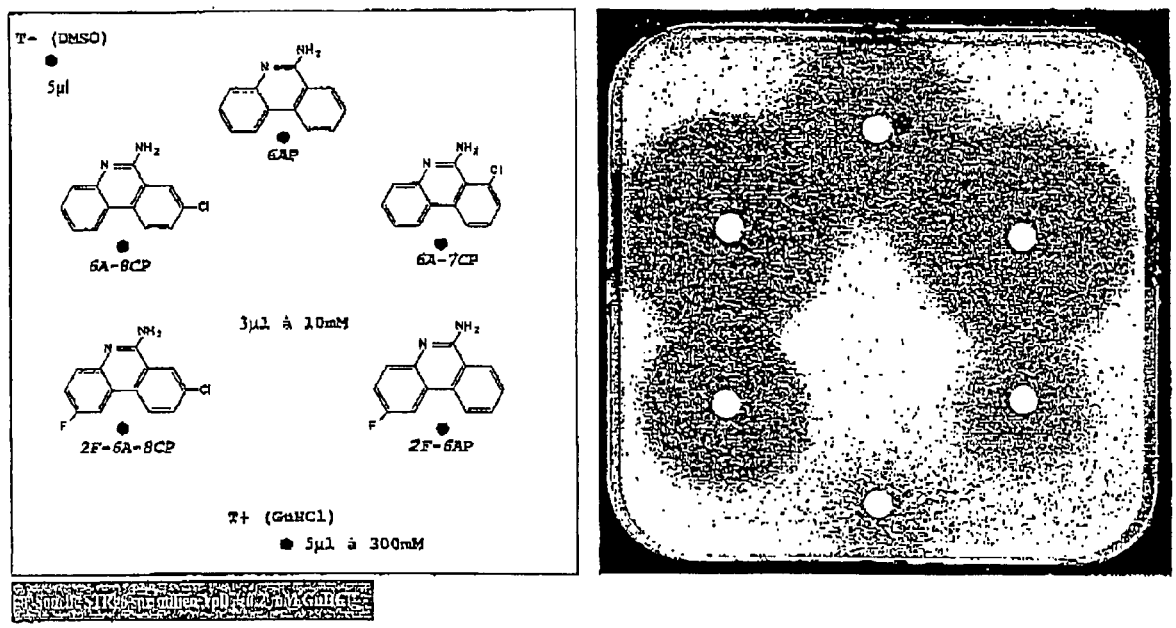

Other characteristics and advantages of the invention will become apparent in the examples below and by referring to the following figures:

FIG. 1 relates to the feasibility of the screen,
FIG. 2 illustrates the screening protocol,
FIG. 3 relates to the isolation of the Kastellpaolitines, phenanthridine and to their structure/activity relationship,
FIG. 4 relates to the determination of the activity of the phenanthridine derivatives,
FIG. 5 shows the results of the liquid curing tests,
FIG. 6 relates to the secondary screen based on the [URE3] prion,
FIG. 7 demonstrates the validation of the test with chlorpromazine, quinacrine and verapamil,
FIG. 8 shows the results of the effect of KP1 on the mammal prion in an in vitro model, and,
FIG. 9 relates to a structure/activity study carried out on the molecule of general formula (II).

EXAMPLE 1

Carrying Out the Screen

1. Material and Methods

Organisms (*Saccharomyces cerevisiae*) and Culture Media

The [PSI+] haploid yeast strain 74-D694 (Mat a, adel-14, trpl-289, his3-Δ200, ura3-52, leu2-3,112) was used in the development of the screening method. The strain used is called "Strong" as it has a well-marked phenotype when the translation termination factor Sup35p is in prion or aggregated form.

In order to increase the penetration of the inhibitors, the inventors genetically modified this strain by introducing into it a mutation of the ERG6 gene. This gene is involved in the biosynthesis of ergosterol, a component of the cell wall of the yeasts. The mutation was produced by insertion at the level of the chromosome site of the ERG6 gene of a "deletion cassette" corresponding to the TRP1 marker gene flanked by DNA sequences situated upstream and downstream of the coding frame of the ERG6 gene. This cassette was produced by PCR using the plasmid pFA6a-kanMX6 as matrix and the oligonucleotides oBM1060 (5') et oBM1061 (3') as primers. The "Strong" 74-D694 yeast cells having integrated the deletion cassette (strain called STRg6, deposited at the CNCM on 10th Oct. 2002 under number 1-2943) are those which develop on minimum media devoid of tryptophan. The mutation Δerg6::TRP1 was then verified by PCR using the genomic DNA of the strain STRg6 as matrix and the oligonucleotides oBM1030 (5') and oBM1063 (3') as primers.

The PCR primers used have the following nucleotide sequences:

(SEQ ID No. 1)
oBM1060 5' CGATTTAAGTTTTACATAATTTAAAAAAACAAGAATAAA
ATAATAATATAGTAGGCAGCATAAGCGGATCCCCGGGTTAATTAA 3'

(SEQ ID No. 2)
oBM1061 5' CTGCATATATAGGAAAATAGGTATATATCGTGCGCTTTA
TTTGAATCTTATTGATCTAGTGAATGAATTCGAGCTCGTTTAAAC 3' oBM1030 5' GGTACCTCGTTCCCGTAC 3'  (SEQ ID No. 3)

oBM1063 5' CAGTCAGAAATCGAGTTCCA 3'  (SEQ ID No. 4)

Unless otherwise indicated, the yeast strains are cultured at 30° C. in rich medium (YPDψ) or in minimum medium. Unless explicitly specified, the percentages correspond to a mass/volume ratio. The gelosed form is obtained by the addition of 2% agar.

YPDψ: 1% yeast extract (FISHER®), 2% peptone (GiBCO®) and 2% glucose;

Minimum medium: 0.175% yeast nitrogen base without amino acid and ammonium sulphate (DiFCO®), 0.75% ammonium sulphate and 2% glucose. This medium is adjusted to pH 6. In order to compensate for possible auxotrophies, this medium can be completed, after sterilization, by the addition of amino acids (0.002% L-histidine and/or 0.004% L-leucine and/or 0.003% L-tryptophan) or nitrogenous bases (0.0025% uracil and/or 0.008% adenine).

Method for screening substances with anti-prion activity ("Prion Halo Assay")

The screening method developed is based on the antibiogram principle. In fact, the compounds to be tested are applied to a sterile filter-paper disc, itself applied to a dish of solid YPDψ medium containing 0.2 mM of guanidium chloride previously seeded with approximately 5·10$^6$ cells of the STRg6 strain in order to produce a yeast lawn. This quantity of seeded cells (from 10$^6$ to 10$^7$) was optimized in order for each cell to be able to divide at least 6 times (number of generations necessary to have an effective curing effect with 3 mM of GuHCl). The addition of a small quantity of guanidium chloride (0.2 mM), a sub-effective dose for eliminating prions from yeast (the effective dose being of the order of 1 to 5 mM) makes it possible to increase the sensitivity of the test (see Results section). The 12 cm square dishes are then incubated for 3 days at 23.5° C. in order to allow the appearance and growth of the yeast colonies. These dishes are then stored for 3 days at 4° C. in order to accentuate the red staining present around the discs soaked with ingredients active on the prion form of the protein Sup35p. Comparison with the negative controls (application of the solvent of the inhibitors tested) and positive controls (application of a 300 mM guanidium chloride solution, causing effective elimination of the Sup35p proteins in prion form) makes it possible to judge the effectiveness of a compound. FIG. 2 illustrates the protocol of the screening method: (1) Culture of the STRg6strain; (2) Application and plating with sterile glass beads 3 & 4 mm in diameter, of approximately 106 cells in exponential growth phase on a dish of solid YPDψ medium containing 0.2 mM of guanidium chloride: constitution of the cell "lawn"; (3) Application of the sterile filter-paper discs according to a grid allowing the analysis of 32 compounds (including controls) and deposit of 20 μl maximum of each of the products to be tested; (4) Incubation; (5) Scanning of the result obtained; (6) Example showing the isolation of a compound having a strong anti-prion activity.

Synthesis of ll-aminodibenzo[b,f][1,4]thiazepines and 6-aminophenanthridine ll-aminodibenzo[b,f][1,4]thiazepines, also called Kastell-paolitines, can be prepared in a single stage. The synthesis of these products has already been described in the publication by Mettey et al., 1997.

2. Results

Principle and Feasibility of the Screen

Guanidium chloride, the only product known to effectively eliminate prions from the yeast *Saccharomyces cerevisiae*, served not only as a positive control throughout screening, but also for studying the feasibility of the method as well as developing it. Guanidium chloride effectively eliminates the different yeast prions at a dose comprised between 1 and 5 mM (Fernandez-Bellot and Cullin, 2001). Under these conditions, the curing requires a constant presence of this product for six to ten generations in exponential growth phase compromising the feasibility of the screen on a dish such as the inventors wished to achieve.

FIG. 1 shows the feasibility of the screen.

The three left-hand panels: a [PSI+] strain is cultured for 48 hours in the presence of 5 mM guanidium chloride (with 0.2% DMSO final) or, as a control, with only 0.2% DMSO final. At T=0, then every 24 hours, a 10 μl drop (approximately 10$^4$ cells) is applied to a dish of rich medium. The guanidium chloride curing begins to have an effect after 24 hours of treatment, i.e. after approximately 6 generations (a pink staining begins to appear). After 48 hours, i.e. after approximately 12 generations, the drop of cells has a clearly red staining, a sign of a complete curing of the [PSI+] cells.

The middle panel: a few cells are taken at T=48 hours and scratched onto a fresh medium. Almost all of them form red colonies in the case of curing with guanidium chloride.

The right-hand panel: these same cells are pelleted at the bottom of an Eppendorf tube after liquid culture. In the case of curing with guanidium chloride, they form a red pellet.

The first stage therefore consisted of determining whether guanidium chloride could have an effect which can be visualized on a dish of [PSI+] cells with the antibiogram pellet system. Once this stage was carried out, the inventors developed the optimum temperature, medium and density conditions as well as cell type to use (FIG. 2). The strain having the best sensitivity is the STRg6 strain cultured at 23.5° C. and in the presence of 200 μM of guanidium chloride. In fact, the introduction of a sub-effective dose of guanidium chloride into the medium makes it possible to increase the sensitivity of the test.

Screening of a Combinatorial Library

Compounds (approximately 1000) were passed through the screen using the conditions optimized by the inventors (FIG. 2). On each dish, 15 μl of DMSO are deposited on the filter at the top left (negative control) and 15 μl of a 300 mM solution of guanidium chloride in DMSO (positive control) were applied to the filter at the bottom right. The same volume (15 μl) of each of the products of the library (all in 10 mM solution in DMSO) was applied to the remaining filters (thirty for each large square Petri dish). A positive signal (visualization of a red halo around the sterile filter-paper disc to which the product is applied) was obtained for five products. These products correspond to four molecules of the same family, called "Kastellpaolitines" by the inventors, and to a well-known fifth molecule: phenanthridine.

EXAMPLE 2

Identification of the Kastellpaolitines and Phenanthridine

The chemical structures of the Kastellpaolitines and phenanthridine are shown in FIG. 3B. The panel 3A shows a comparative analysis of the size of the red halos obtained with all of these molecules respectively (all applied in an equivalent quantity: 15 µl of a 10 mM solution in DMSO). This experiment makes it possible to compare the relative activity of each of these products. The most active is Kastellpaolitine 1 (or KP1) followed by phenanthridine.
6-aminophenanthridine Synthesis and Test Comparative analysis of phenanthridine on the one hand, and of the Kastellpaolitines on the other hand show several common points between these two groups of molecules (FIG. 3). The different molecules are classified there from the least active to the most active and their respective formulae indicated. All are tri-cyclic, the central ring containing in all cases a nitrogen atom with a double bond to an adjacent carbon atom. In contrast, in all the Kastellpaolitines, the carbon of the central ring which has a double bond to this nitrogen atom carries an amino group, which is not the case for phenanthridine. This observation led the inventors to want to test 6-aminophenanthridine.

6-aminophenanthridine can be prepared according to the procedure developed by Kessar et al., 1969.

6-aminophenanthridine was therefore passed through the screen according to the invention, in comparison with the Kastellpaolitines 1 (KP1) and 5 (KP5) as well as phenanthridine. The result is very clear: 6-aminophenanthridine is still more active than the Kastellpaolitines and phenanthridine.

FIG. 4 illustrates the results of this comparison: the activity of 6-aminophenanthridine was determined on a dish and compared to that of phenanthridine. For all the molecules, the same quantity is applied (10 µl of a 10 mM solution). In the case of the positive control (guanidium chloride), the solution used was 300 mM.

As a result, by grafting this amino group, characteristic of the Kastellpaolitines onto phenanthridine, the inventors significantly increased the activity of the latter.

By following the same approach, the inventors then added a chlorine in position 8 in 6-aminophenanthridine (6AP) in order to produce 6-amino-8-chlorophenanthridine (6A-8CP). This modification again increased the activity of the compound. Finally, the chlorine in position 8 was replaced by a trifluoromethyl group in order to produce 6-amino-8-trifluoromethylphenanthridine (6A-8tFP). As shown by FIG. 4, the latter modification led to an additional increase in activity and 6A-8tFP in fact represents one of the most active compounds.

EXAMPLE 3

Synergy Between Products Isolated Using the Screen and Guanidium Chloride

All the active molecules were isolated in a medium containing a weak dose of guanidium chloride (200 µM/effective dose=4 mM). Taking this course, established during the development of the screen corresponded to the wish to increase the sensitivity (and therefore the detection threshold of the method). The effect of the molecules in media containing more (500 µM) guanidium chloride or not containing any, was observed subsequently. Phenanthridine is always active on a medium without guanidium chloride, but its activity increases significantly as a function of the quantity of guanidium chloride (however in a clearly sub-effective dose) in the medium. This result indicates a synergy of action between guanidium chloride and phenanthridine. The same result was obtained for all the other molecules isolated by the inventors (the Kastellpaolitines, 6-aminophenanthridine and its derivatives).

EXAMPLE 4

Verification of Liquid Medium Curing

The inventors then wanted to determine whether the red halos observed in the yeast test corresponded to [PSI+] prion curing and not to an artefact (for example these red halos could be due to a direct inhibition of the biosynthesis chain of adenine by these molecules, which would lead to a accumulation of the AIR). If these molecules effectively eliminate the [PSI+] prion, a treatment of [PSI+] cells in liquid culture followed by washing of said cells must allow them to form red colonies on a gelosed medium no longer containing the molecules. These tests were carried out with 6-aminophenanthridine on the wild-type "strong" strain 74-D694.

The liquid medium curing conditions are the following: a [PSI+] strain is cultured for 5 days in liquid medium in the presence of the indicated quantities of the different products (see FIG. 5). Every 24 hours, an aliquot fraction is washed in medium uncontaminated by any product and applied to a solid gelosed medium (itself also uncontaminated by any product) which is then treated as indicated in FIG. 2.

As shown in FIG. 5, 6-aminophenanthridine is capable of partially curing the [PSI+] prion from a significant number of cells. The curing effectiveness can in particular be increased by adding a sub-effective dose (100 µM) of guanidium chloride to the culture medium. In such a liquid curing, the same synergic effect as that observed in the dish test is also found.

EXAMPLE 5

Development and Use of a Secondary Calorimetric Screen Based on the Use of [URE3], Another Yeast Prion Another rapid dish test was carried out, based on another yeast prion: [URE3]. This test constituted a secondary screen which makes it possible to generalize the effect of the products isolated during the primary screen of another yeast prion. In this way, it is possible to remove the molecules active only against the [PSI+] prion and therefore less useful, having a non-general effect.

For the [URE3] prion the haploid strain used is CC34 (Mat a, trpl-1, ade2-1, leu2-3,112, his3-11, 15, ura2:: HIS3).

The NT34 strain which served for the secondary screen was constructed from CC34, a strain in which the coding frame of the DAL5 gene has been replaced by that of the ADE2 gene using the same method as that used for the construction of the STRg6 strain. For this purpose a deletion cassette corresponding to the ADE2 gene flanked by DNA sequences situated upstream and downstream of the coding frame of the DAL5 gene was produced by PCR using genomic DNA of the BY4742 haploid strain (Mat α, his3Δ1, leu2Δ0, lys2Δ0, ura3Δ0) as matrix and the oligonucleotides: ACAACAAAACAAGGATAATCAAATAGTG-TAAAAAAAAAAATTCAAGATGGATTCTAG AACAGT-TGG (SEQ ID No. 5) (5'), and TATATTCTTCTCTGATAA- CAATAATGTCAGTGTATCTCACCACTATTATTACTTGTT TTCTAGATAAGC (SEQ ID No. 6) (3') as primers.

The mutation DAL5::ADE2 was then verified by PCR using the genomic DNA of the NT34 strain as matrix and the oligonucleotides:

ATAGTCTCTGCTCATAG (SEQ ID No. 7) (5'), and GCT-TACAGAAATTCTAC (SEQ ID No. 8) (3') as primers.

The NT34 strain (Mat a, trpl-1, ade2-1, leu2-3,112, his3-11,15, ura2::HIS3, DAL5::ADE2) was deposited at the CNCM on 10th Oct. 2002 under number 1-2942.

This screen is based on the same colorimetric system as the primary screen. In the NT34 yeast strain, the ADE2 gene is no longer under the control of its own promoter, but under that of the DAL5 gene. When the protein Ure2p is in prion form ([URE3]), the transcription from the promoter of the DAL5 gene is activated, therefore the ADE2 gene is expressed, therefore the strains are white and autotrophic for adenine. When the URE2p protein is in the normal form ([URE3-0]), the transcription from the promoter of the DAL5 gene is repressed, therefore the ADE2 gene is not expressed, therefore the strains are red and auxotrophic for adenine. When the NT34 strain is treated with 5 mM of guanidium chloride for approximately ten generations, it forms red colonies (as expected and as the [PSI+] strain used for the primary screening would do). As can be observed in FIG. 6, phenanthridine and 6-aminophenanthridine cause the appearance of a red halo when they are applied to the small filter itself applied to the lawn of cells previously plated on the gelosed nutritive medium (same process as for the primary screen, see FIG. 2). This result suggests that these products are also active on the [URE3] prion. It is to be noted, however, that this secondary screen is clearly less sensitive than the primary screen. It is therefore very useful for rapidly observing whether the effect of the molecules isolated during the first screen can be generalized to other yeast prions but in no event could it be substituted for the primary screen.

In order to increase cell permeability, the coding sequence of the ERG6 gene was also replaced by that of the TRP1 gene. In this strain (SB34), the transcription of ADE2 therefore depends on the state of Ure2p: if Ure2p is inactivated by a prion mechanism ([ure3] cells), the ADE2 gene is actively transcribed whereas in the [ure 3-0] cells, it is not. Therefore, the [URE3] cells of the SB34 strain will form white colonies whereas the [ure3-0] cells will form red colonies. Because this strain always contains the ade2-1 allele, it was envisaged that this strain could be [PSI+], such that the red staining could be due to the curing of [PSI+] rather than of [URE3]. This possibility has been excluded by verifying using cytoduction and conjugation that the strain is [URE3]. Moreover, the entire coding sequence of the ade2-1 gene was deleted in order to produce the NT35 strain. This strain also formed white colonies, demonstrating again that it is [URE3].

The SB34 strain was constructed by replacing the ERG6 gene in CC34 by PCR amplification of the TRP1 marker and by replacing the coding region of the DAL5 gene by the ADE2 gene using a method based on PCR by deletion of the ERG6 gene with the primers (5'-ACAACAAAACAAG-GATAATCAAATAG TGTAAAAAAAAAAATTCAA-GATGGATTCTAGAACAGTTGG-3') (SEQ ID No. 9) and 342 (5'-TATATTCTTCTCTGATAACAATAATGT-CAGTGTATCTCACCA CTATTATTACTTGTTTCTA-GATAAGC-3') (SEQ ID No. 10). This gene replacement was then confirmed by growth on the SD-Ade medium, in the absence of growth on the USA medium (as provided for a dal5Δ strain) and by analytic PCR on the genomic DNA. The [URE3] phenotype of this strain was verified by cytoduction: among 30 cytoduction agents, 26 were capable of growing on USA medium, showing that they were [URE3]. The NT35 strain was constructed by replacing the ade2-1 gene in the SB34 strain by the marker KanMX amplified by PCR and by verifying the successful replacement of the gene by analytic PCR on the genomic DNA.

EXAMPLE 6

Verification of Liquid Medium [URE3] Curing

Two types of experiments were carried out in order to verify that the effect observed on dishes with the NT34 strain corresponds to curing. Firstly, cells in the zones surrounding the filter were recovered for the negative (DMSO), and positive (guanidium chloride) control for phenanthridine and for 6-aminophenanthridine. These cells were then scratched onto a fresh medium free of all these molecules. The cells recovered around the filters all form red colonies, with the exception of those collected around the negative control. This result shows that the red staining observed on dishes for the NT34 strain corresponds to curing and not to an artefact linked to inhibition of an enzyme of the biosynthesis route of adenine (in this case, the red staining would be lost on a medium without inhibitor). The curing effect of phenanthridine and 6-aminophenanthridine was also directly verified on the [URE3] prion. [URE3] cells of the CC34 strain grow on a medium called USA whereas cured ([ure3-0]) cells are incapable of growing on this medium. The inventors examined the ability of [URE3] cells treated with 200 μM of guanidium chloride (negative control), 5 μM of guanidium chloride (positive control) or with different doses of 6-aminophenanthridine (alone or in combination with 200 μM of guanidium chloride) to grow on a USA medium. 6-aminophenanthridine is capable of curing the [URE3] prion in a significant manner and, just as for the [PSI+] prion, this effect is accentuated by a low dose of guanidium chloride (200 μM). These results, apart from the fact that they validate the secondary screen with the NT34 strain, suggest that the effect of the inhibitors revealed by said screen should be general on all yeast prions.

EXAMPLE 7

Validation of the Screen with Two Molecules Active on the Mammal Prion PrP: Chlorpromazine and Guinacrine The laboratory of Stanley Prusiner, who first put forward the "protein-only" hypothesis and was awarded the Nobel prize in 1997, has isolated a certain number of molecules active on the mammal prion PrP using a system of murine cells (neuroblastomas) chronically infected with the prion PrP$^{sc}$ (Korth et al., 2001). This system, due to its labour-intensiveness and its complexity, does not allow mass screening like that developed by the inventors. Thus the approach of Stanley Prusiner's group was to test one-by-one, from the molecules already used as medicaments, those which pass the blood-brain barrier. Certain molecules, such as in particular quinacrine (used as an anti-malarial drug for a long time) or chlorpromazine (an antidepressant) have a particular activity in their system. In order to validate the screen, the inventors therefore tested chlorpromazine and quinacrine in their yeast system. As shown in FIG. 7, these two molecules have a certain activity against the [PSI+] prion. It must however be noted that their activities are clearly weaker than that of 6-aminophenanthridine. It can also be seen that chlorpromazine and quinacrine, like all of the molecules highlighted by the invention, exhibit a strong synergy of action with guanidium chloride (In FIG. 7, the medium used contains 200 μM of guanidium chloride) The latter result suggests that these two molecules act on the same biochemical route as the isolated molecules according to the invention.

Moreover, it is interesting to note that quinacrine, the activity of which is approximately ten times greater than that of chlopromazine in Prof. Prusiner's test, also exhibits an activity greater than the latter in the screen developed by the inventors. Moreover, just as in Prof. Prusiner's test, chlorpromazine and quinacrine require prolonged treatment (at least 6 days in the case of Prof. Prusiner's test, at least two to three days in the case of the screen according to the invention) before an activity is detected.

Moreover, the inventors determined the activity, in the test according to the invention, of other molecules isolated using the test based on mouse neuroblastomas, developed by Prof. Prusiner. A good correlation was found between the results obtained in the two systems: acepromazine which is shown to be slightly active in the mammal system also exhibits a weak activity in the test according to the invention and the molecules inactive in analysis on mammals such as carbamazepine, imipramine, haloperidol, chloroprothixene or methylene blue were also inactive in the test.

Quinacrine has also been described as an inhibitor of multiple drug resistance (MDR). In order to test whether its anti-prion effect could involve this mechanism (which is compatible with the synergic effect of GuHCl), we evaluated the putative curative effect of an effective general inhibitor of MDR, verapamil. As shown by FIG. 7, although a strong concentration of this medicament was used, a concentration close to toxicity, no curative effect could be detected.

All these correlations between the activity of quinacrine and chlorpromazine according to the test or the screen used make it possible to validate the use of the method according to the invention in order to carry out high-throughput screenings with a view to isolating molecules capable of constituting effective medicaments (on mammals and in particular humans) against neurodegenerative diseases involving protein aggregates, of spongiform-encephalopathy type, Alzheimer's disease, Huntington's disease etc.

EXAMPLE 8

Analysis of the Inhibition of PrP$^{sc}$ in ScN2a-22L Cells

Mouse neuroblastoma cells infected with the scrapie prion (ScN2a-22L) were used. The cells were cultured in 25 cm$^2$ flasks in the presence or absence of the compounds for several days. Then, the proteins were extracted from the ScN2a-22L cells by cell lysis in 500 µl of lysis buffer (50 mM of Tris HCl pH 7.5; 150 mM of NaCl, 0.5% sodium deoxycholate; 0.5% Triton X100). After normalization of the proteins with the Uptima Interchim kit, the adjusted quantities of cell lysates were digested by proteinase K at 20 µg/ml (Eurobio) for 40 minutes at 37° C. The lysates were then centrifuged for 90 minutes at 20,000×g and the pellet was resuspended in 25 µl of denaturing buffer (1 X Tris-Glycine; 4% of SDS, 2% of β-mercaptoethanol; 5% of sucrose and bromophenol blue) and heated for 5 minutes at 100° C. before Western blot analysis according to the standard protocol using the mouse monoclonal antibody anti-PrP SAF83 (supplied by SPI-BIO, Massy-Palaiseau, France). The percentages of inhibition of the formation de PrP$^{sc}$ resistant to proteinase K were calculated using NIH Image J: the inhibition of the accumulation of PrP$^{sc}$ was 96% for chlorpromazine (Chlor. ) and 70%+/−6% for KP1.

Two of the compounds selected (KP1 and 6AP) were tested in this mammal system. As shown by FIG. 8, KP1 was capable of inducing a significant reduction in the accumulation of mammal prion at a dose similar to that used for chlorpromazine (5 µM). After 7 days of treatment, 70% of the PrP$^{sc}$ resistant to proteinase K have disappeared (wells 1 to 3) compared with untreated cells (wells 4 and 5). This significant effect was probably under-estimated since the cells treated with the solvent of the compounds alone (DMSO 0.01%) showed a significant and reproducible rise in PrP$^{sc}$ resistant to proteinase K (well 6). The same effect on the elimination of PrP$^{sc}$ was obtained with 6AP at 2 and 4 µM.

These results therefore validate the use of the screening test according to the invention based on yeast in order to isolate anti-prion compounds since quinacrine and chlorpromazine were detected using this analysis and KP1 and 6AP were also effective in promoting the elimination of the mammal prion in vitro.

EXAMPLE 9

Study Structure/Activity

For the purpose of studying the different substitution positions of the anti-prion molecules isolated, the inventors carried out a structure/activity study on the 6-aminophenanthridine molecule. 2-fluoro-6-aminophenanthridine (2F-6AP), 2-fluoro-6-amino-8-chlorophenanthridine (2f-6A-8ClP) and 6-amino-7-chlorophenanthridine (6A-7ClP) molecules were thus obtained by chemical synthesis and their anti-prion activity was determined using the test according to the invention. The results obtained are shown in FIG. 9. The diameters of the red halos obtained being proportional to the anti-prion activity of the molecules deposited, the results indicate that the presence of a halogen-type substituent at the level of positions 7 or 8 increases the anti-prion activity of the molecules of formulae (II) whereas the same type of substituent in position 2 tends to reduce it.

Bibliographical References

Fernandez-Bellot et al., "*The protein-only theory and the yeast Saccharomyces cerevisiae: the prions and the propagons*", CMLS, 2001, 58: 1857-1878.

Korth C. et al., "*Acridine and phenothiazine derivatives as pharmacotherapeutics for prion disease*", PNAS, 2001, 98(17): 9836-9841.

Mettey Y. et al., "*Synthesis of 11-Aminodibenzo[b,f][1,4] thiazepines and Fluoro derivatives*", J. Heterocyclic Chem., 1997, 34: 465-467.

Kessar S. V. et al., Tetrahedron Letters, 1969, 1151.

The invention claimed is:

1. A pharmaceutical composition comprising:
a therapeutically effective quantity of at least one compound of formula (II)

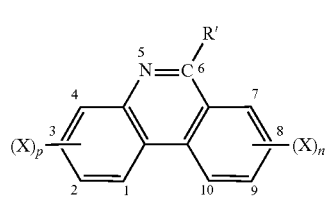

(II)

wherein R' represents an $NH_2$, or $NH-CH(CH_3)-(CH_2)_3-N(CH_2-CH_3)_2$ group,
X represents F, Cl, or $CF_3$,
p and n, identical or different, are equal to 0, 1 or 2,
in combination with at least one pharmaceutically acceptable vehicle.

2. The pharmaceutical composition of claim 1 wherein in the compound of formula (II), R' represents an $NH_2$ group,
X represents F, Cl, or $CF_3$,
p and n, identical or different, are equal to 0, 1 or 2.

3. A pharmaceutical composition comprising:
a therapeutically effective quantity of at least one compound of formula (II)

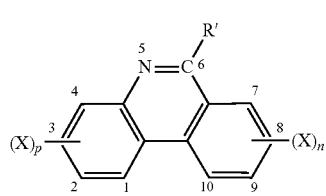

(II)

wherein R' is $-NH-(CH_2)_3-N(CH_3)_2$,
X is F, Cl, or $CF_3$, and
p and n, identical or different, are equal to 1 or 2,
in combination with at least one pharmaceutically acceptable vehicle.

* * * * *

SEQUENCE LISTING

<160> NUMBER OF SEQ ID NOS: 10

<210> SEQ ID NO 1
<211> LENGTH: 84
<212> TYPE: DNA
<213> ORGANISM: Artificial sequence

```
<220> FEATURE:
<223> OTHER INFORMATION: primer

<400> SEQUENCE: 1
cgatttaagt tttacataat ttaaaaaaac aagaataaaa taataatata gtaggcagca    60
taagcggatc cccgggttaa ttaa                                           84

<210> SEQ ID NO 2
<211> LENGTH: 84
<212> TYPE: DNA
<213> ORGANISM: Artificial sequence
<220> FEATURE:
<223> OTHER INFORMATION: primer

<400> SEQUENCE: 2
ctgcatatat aggaaaatag gtatatatcg tgcgctttat ttgaatctta ttgatctagt    60
gaatgaattc gagctcgttt aaac                                           84

<210> SEQ ID NO 3
<211> LENGTH: 18
<212> TYPE: DNA
<213> ORGANISM: Artificial sequence
<220> FEATURE:
<223> OTHER INFORMATION: primer

<400> SEQUENCE: 3
ggtacctcgt tcccgtac                                                  18

<210> SEQ ID NO 4
<211> LENGTH: 20
<212> TYPE: DNA
<213> ORGANISM: Artificial sequence
<220> FEATURE:
<223> OTHER INFORMATION: primer

<400> SEQUENCE: 4
cagtcagaaa tcgagttcca                                                20

<210> SEQ ID NO 5
<211> LENGTH: 66
<212> TYPE: DNA
<213> ORGANISM: artificial sequence
<220> FEATURE:
<223> OTHER INFORMATION: primer

<400> SEQUENCE: 5
acaacaaaac aaggataatc aaatagtgta aaaaaaaaaa ttcaagatgg attctagaac    60
agttgg                                                               66

<210> SEQ ID NO 6
<211> LENGTH: 69
<212> TYPE: DNA
<213> ORGANISM: Artificial sequence
<220> FEATURE:
<223> OTHER INFORMATION: primer

<400> SEQUENCE: 6
tatattcttc tctgataaca ataatgtcag tgtatctcac cactattatt acttgttttc    60
tagataagc                                                            69

<210> SEQ ID NO 7
<211> LENGTH: 17
<212> TYPE: DNA
<213> ORGANISM: Artificial sequence
```

```
<220> FEATURE:
<223> OTHER INFORMATION: primer

<400> SEQUENCE: 7
atagtctctg ctcatag                                                  17

<210> SEQ ID NO 8
<211> LENGTH: 17
<212> TYPE: DNA
<213> ORGANISM: Artificial sequence
<220> FEATURE:
<223> OTHER INFORMATION: primer

<400> SEQUENCE: 8
gcttacagaa attctac                                                  17

<210> SEQ ID NO 9
<211> LENGTH: 66
<212> TYPE: DNA
<213> ORGANISM: Artificial sequence
<220> FEATURE:
<223> OTHER INFORMATION: primer

<400> SEQUENCE: 9
acaacaaaac aaggataatc aaatagtgta aaaaaaaaaa ttcaagatgg attctagaac    60
agttgg                                                              66

<210> SEQ ID NO 10
<211> LENGTH: 68
<212> TYPE: DNA
<213> ORGANISM: Artificial sequence
<220> FEATURE:
<223> OTHER INFORMATION: primer

<400> SEQUENCE: 10
tatattcttc tctgataaca ataatgtcag tgtatctcac cactattatt acttgtttct    60
agataagc                                                            68
```